United States Patent
Brunner et al.

(10) Patent No.: US 6,346,629 B1
(45) Date of Patent: Feb. 12, 2002

(54) METHOD FOR PRODUCING BUTYROLACTONES

(75) Inventors: Melanie Brunner, Schifferstadt; Ralf-Thomas Rahn, Mannheim; Udo Rheude, Otterstadt; Jochem Henkelmann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,426

(22) PCT Filed: May 21, 1999

(86) PCT No.: PCT/EP99/03506

§ 371 Date: Nov. 15, 2000

§ 102(e) Date: Nov. 15, 2000

(87) PCT Pub. No.: WO99/62895

PCT Pub. Date: Dec. 9, 1999

(30) Foreign Application Priority Data

Jun. 3, 1998 (DE) .......................... 198 24 534

(51) Int. Cl.$^7$ ............................ C07D 307/02
(52) U.S. Cl. .................. 549/295; 549/214; 549/323; 549/324
(58) Field of Search ................. 549/295, 214, 549/323, 324

(56) References Cited

U.S. PATENT DOCUMENTS

| | | | |
|---|---|---|---|
| 3,547,964 A | 12/1970 | Olivier | 260/429 |
| 4,400,547 A | 8/1983 | Dawes et al. | 568/454 |
| 4,473,655 A | 9/1984 | Tsunoda et al. | 502/24 |
| 5,364,445 A | 11/1994 | Sakamoto et al. | 75/426 |
| 5,962,700 A | 10/1999 | Heider et al. | 549/295 |

FOREIGN PATENT DOCUMENTS

| | | |
|---|---|---|
| CA | 2104509 | 3/1994 |
| DE | 32 01 723 | 8/1982 |
| DE | 43 26 076 | 3/1994 |
| EP | 429 963 | 6/1991 |
| EP | 584 720 | 3/1994 |
| WO | 97/07111 | 2/1997 |

OTHER PUBLICATIONS

Inorganica Chim.Acta, 220(1994) 45–53, Joh et al.

Primary Examiner—Amelia Owens
(74) Attorney, Agent, or Firm—Keil & Weinkauf

(57) ABSTRACT

Process for producing butyrolactones of the general formula I

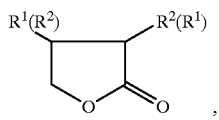

I where $R^1$ and $R^2$ are each hydrogen, alkyl, hydroxyalkyl, substituted or unsubstituted aryl or substituted or unsubstituted trialkylsilyl, by reacting alkynes of the general formula II

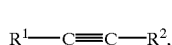

II where $R^1$ and $R^2$ are each as defined above, with carbon monoxide and water in the presence of a rhodium catalyst under pressures from 20 to 300 bar and hydrogenating the unhydrogenated 2(5H)-furanone intermediates comprises a) reacting the carbonylation reaction mixture with hydrogen at from 150 to 250° C. and from 100 to 300 bar,
b) removing the precipitated catalyst and returning it into the carbonylation reaction, and
c) subjecting the catalyst-free reaction mixture to a distillation to recover the butyrolactone.

10 Claims, No Drawings

METHOD FOR PRODUCING BUTYROLACTONES

The present invention relates to a process for producing butyrolactones by carbonylating alkynes with carbon monoxide in the presence of water over a rhodium catalyst and precipitating the rhodium catalyst by immediate hydrogenation of the carbonylation reaction mixture, removing and recycling the catalyst and recovering the butyrolactone from the filtrate.

WO 97/07111 discloses reacting alkynes with carbon monoxide and water in the presence of transition metal catalysts, especially rhodium, to obtain butyrolactones. As stated by Takaski Joh et. al. in Inorganica Chi. Acta, 220 (1994) 45, 2(5H)-furanones are formed as intermediates. The 2(5H)-furanones can be converted into butyrolactones by hydrogenation in situ or separately. Complete hydrogenation to butyrolactones is obtained by forcing the carbonylation reaction in the presence of water, which may give rise to hydrogen as a result of the water gas equilibrium, by adding hydrogen during the carbonylation, or by subsequent hydrogenation of the isolated 2(5H)-furanones.

However, the butyrolactone production process of WO 97/07111 has proved unsatisfactory with regard to catalyst removal and reuse. True, after the synthesis effluent has been worked up, i.e., the butyrolactones have been recovered by distillation, the dissolved catalyst remaining behind in the distillation residue can be reused. But this has the disadvantage that, on the one hand, the catalyst cannot be separated from the distillation residue and therefore there will be a buildup of high boilers in the course of repeated recycling, and, on the other, the repeatedly reused catalyst provides distinctly reduced selectivity and activity with regard to the desired conversion into butyrolactones.

There is therefore a need for a simple process for isolating ideally all the rhodium carbonylation catalyst without loss of activity for recycling into the reaction.

Numerous processes have been described for removing rhodium in the field of hydroformylation. In U.S. Pat. No. 4,400,547 the crude oxo product is contacted after the reaction with a ligandizing compound such as triphenylphosphine and the aldehyde is distilled off as product. The distillation residue is then treated with oxygen to deligandize the catalyst and recover the rhodium in an active form. However, this does not provide a way of separating rhodium and distillation residue.

The removal of rhodium from high boiling hydroformylation residues is also described in U.S. Pat. No. 3,547,964. The residues are treated with hydrogen peroxide in the presence of acids such as formic acid, nitric acid or sulfuric acid to convert the rhodium into a water-soluble form. However, the cost of hydrogen peroxide and its problematical handling put limits on the use of this technique in industry.

EP-A 584 720 B1 discloses an optionally two-stage extraction process wherein rhodium is recovered in the form of a complex from the distillation residues of products of the oxo process. In the first stage, the residues are treated with oxygen or an oxygen-containing gas in the presence of a monocarboxylic acid and of the alkali metal salt of the monocarboxylic acid. The residue is then extracted with water, and the rhodium, which is present as a water-soluble compound, passes into the aqueous phase. This process is not practicable in the present case, since the rhodium complex has proven to be difficult to extract quantitatively from the butyrolactone synthesis reactor effluent.

Other processes, for example as described in DE-A 43 26 076, concern the recovery of rhodium by ashing, i.e., burning, the organic constituents. The rhodium thus recovered cannot be reused immediately, but requires a further workup.

It is an object of the present invention to provide a simple and economical process for isolating ideally all the rhodium carbonylation catalyst without loss of activity for recycling into the reaction.

We have found that this object is achieved, surprisingly, by a process for producing butyrolactones of the general formula I

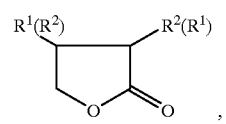

where $R^1$ and $R^2$ are each hydrogen, alkyl, hydroxyalkyl, substituted or unsubstituted aryl or substituted or unsubstituted trialkylsilyl, by reacting alkynes of the general formula II

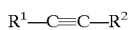

where $R^1$ and $R^2$ are each as defined above, with preferably not less than 4 equivalents of carbon monoxide and preferably not less than 2 equivalents of water in the presence of a rhodium catalyst under pressures from 20 to 300 bar and hydrogenating the unhydrogenated 2(5H)-furanone intermediates, which comprises a) reacting the carbonylation reaction mixture immediately (i.e., without removal of the 2(5H)-furanone target product or of a mixture thereof with butyrolactone) with hydrogen at from 150 to 250° C.; preferably from 180 to 230° C., and from 100 to 300 bar, preferably from 150 to 200 bar, b) removing the precipitated catalyst and returning it into the carbonylation reaction, and c) subjecting the catalyst-free reaction mixture to a distillation to recover the butyrolactone.

Surprisingly, more than 99% of the catalyst used is recovered and even frequent repetition of the operation or a prolonged continuous run does not harm the selectivity and activity of the catalyst.

True, WO 97/07111 states in paragraph 5 on page 7 that it can be sensible to produce only mixtures comprising predominantly butyrolactone. These mixtures can then be fed "directly" into the hydrogenation or be separated into their individual components, butyrolactone and furanone. However, there is no teaching in the cited reference that hydrogenating the reaction mixture while it still contains the catalyst will under certain conditions precipitate the catalyst, which may then be removed and returned into the reaction. On the contrary, the only relevant example (8) utilizes a specific hydrogenation catalyst, in fact a palladium catalyst, to hydrogenate the 2(5H)-furanone at atmospheric pressure and room temperature only after it has been freed from catalyst.

For stage (a) of the process of the invention, the carbonylation reaction mixture is subjected to a hydrogenation with hydrogen at pressures from 20 to 300 bar, preferably from 150 to 250 bar, especially from 180 to 220 bar, immediately after the residual CO pressure has been released, without prior removal of the 2(5H)-furanone intermediates formed or of the butyrolactones already formed. The hydrogenation converts the rhodium carbonyl catalyst into an insoluble form (it is believed through removal of some of the carbonyl groups and, it is believed, through formation of a rhodium cluster) and the 2(5H)-furanones to the corresponding butyrolactones. The reaction temperature for the hydrogenation is generally within the range from 0 to 300° C., preferably within the range from 50 to 150° C., while the reaction time for the hydrogenation is generally within the range from 0.1 to 24 h, preferably within the range from 0.5 to 5 hours.

The reaction gives rise to a solid material which contains the catalyst and which can be removed by common methods such as, for example, filtration, centrifugation or sedimenting. At the same time, any 2(5H)-furanone present is completely and very selectively hydrogenated to the butyrolactone. The precipitated catalyst can be used for renewed butyrolactone syntheses without significant loss of activity or selectivity. The sequence of carbonylation/catalyst precipitation/catalyst removal/ carbonylation can be repeated more than once. The precipitation of the catalyst is virtually quantitative each time; the reactor effluent contains less than 1% of the initial rhodium in homogeneous solution.

The process of the invention is useful for all catalysts suitable for the butyrolactone synthesis described. Preference is given to the catalysts $Rh_6(CO)_{16}$, $Rh_4(CO)_{12}$, $Rh(CO)_2acac$, $[codRhCl]_2$, $RhCl_3*3H_2O$ and $Rh(OAc)_3$.

The amount of catalyst used is generally within the range from 0.01 to 10 mmol per mole of alkyne. The precipitated, removed and recycled catalysts are present as compounds of unknown structure; however, they redissolve in the carbonylation stage and reacquire their earlier activity. Fresh catalyst is added to the reaction solution to the degree that removal is incomplete.

In the preferred continuous carbonylation process detailed in WO 97/07111, the reaction with actylene can be carried out by dissolving acetylene in a solvent in a saturator. The catalyst, water and additives are likewise dissolved. This solution is compressed to the reaction pressure and pumped into the reactor.

CO and further acetylene are introduced into the reactor via a gas jet. The reactor effluent is decompressed and the gas phase may be returned into the reactor, if necessary after a purifying operation. According to the invention, the carbonylation reactor effluent is compressed to the hydrogenation reaction pressure and pumped into a pressure-resistant reactor, such as a stirred, tubular or loop reactor. Hydrogen is introduced into the reactor via a gas jet and the hydrogenation reaction effluent is decompressed on leaving the reactor. A conventional method such as standard filtration, cross-flow filtration, sedimentation or centrifugation can be used to continuously or discontinuously remove the rhodium precipitate formed in the course of the hydrogenation. The solid is then reused as catalyst. The hydrogen gas phase may be returned into the hydrogenation reactor, if necessary after a purifying operation.

The carbonylation of alkynes in the presence of water is carried out in a conventional manner, as extensively described in WO 97/07111.

The alkynes of the formula II may bear identical or different substituents. Different substituents may each end up in positions 3 and 4 of the reaction product. Isomer mixtures are thus likely in these cases. For this reason, formula I depicts alternatives for the substituents in positions 3 and 4.

Alkynes II may bear alkyl groups, for example $C_1$–$C_8$-alkyl groups as in propyne, 1-butyne, 2-butyne, 1-hexyne and 1-octyne.

Hydroxyalkyl substituents on the alkynes are preferably hydroxy-$C_1$–$C_4$-alkyl groups, as in 1-butyn-3-ol, 1,4-butynediol and propargyl alcohol. Of the aryl-bearing alkynes, phenylalkynes are preferred, e.g., phenylacetylene and diphenylacetylene. The aryl groups may bear reaction-inert substituents such as halogen, especially chlorine, alkoxy, especially methoxy, and alkyl, especially $C_1$–$C_4$-alkyl. Suitable alkynes further include alkynes bearing trialkylsilyl groups, such as trimethylsilylacetylene.

Preference is given to those alkynes in which at least one of $R^1$ and $R^2$ is hydrogen. Acetylene is particularly preferred.

The conversion of the alkyne into butyrolactone is carried out in the presence of CO and water:

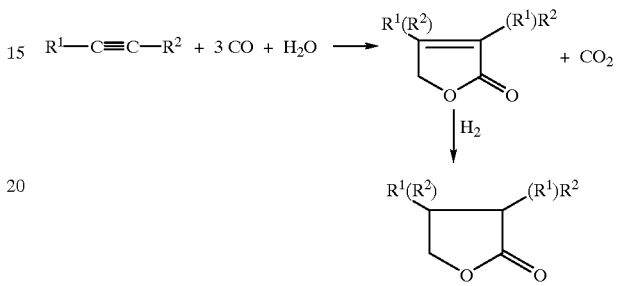

Preference is given to using from 2 to 50 equivalents of water per equivalent of alkyne. It is advisable to use at least 4 equivalents of CO per equivalent of alkyne. CO can also be used in excess, in which case, however, the excess of CO used, based on the alkyne, should generally not exceed 50 times, since still larger excesses do not convey any discernible technical benefits.

The carbonylation can be carried out under the temperature and pressure conditions described in WO 97/07111. However, it has been found to be advantageous to employ rather higher pressures when practicing the process of the present invention. Accordingly, the carbonylation is generally carried out at from 50 to 250° C., preferably from 80 to 150° C., especially at from 100 to 140° C., and from 20 to 300, preferably from 100 to 250, especially from 170 to 230, bar.

The catalysts to be used according to the invention are water gas shift catalysts (see Parshall et al., Homogeneous Catalysis, Wiley, 2nd edition 1992, chapter 5.7) capable of establishing the water-gas equilibrium according to the following equation:

$$CO+H_2O \rightarrow H_2+CO_2$$

The hydrogen which is liberated is thus able to hydrogenate the 2(5H)-furanone intermediate to the butyrolactone.

Additives may be used to increase the activity of the catalysts used. Suitable additives include amines. Suitable amines include primary, secondary and tertiary alkylamines and cycloalkylamines and also nitrogenous heterocycles. Specific examples are methylamine, ethylamine, aniline, diethylamine, triethylamine, tributylamine, trioctylamine, pyridine, quinoline, isoquinoline and dimethylaminopyridine. Ammonium salts such as triethylammonium hydrochloride, tetraethylammonium chloride, tetrabutylammonium acetate, tetrabutylammonium nitrate and tetrabutylammonium hydroxide are also efficaceous.

Suitable additives further include halides. Specific halides which may be used are alkali metal and alkaline earth metal halides, such as NaCl, NaBr, NAI, KCl, KI, $CaCl_2$, $CaBr_2$, $CaI_2$, and also halides with organic cations such as tetramethylammonium chloride, tetramethylammonium bromide, tetramethylammonium iodide, tetrabutylammonium chloride, tetrabutylammonium bromide and tetrabutylammonium iodide. Iodides are preferred halides.

Suitable additives further include polymerization inhibitors for olefinically unsaturated organic compounds such as hydroquinone monomethyl ether, 2,6-di-tert-butyl-4-methylphenol and phenothiazine.

None of these additives interferes with the recovery of the catalyst.

The amount of additive used may be varied within wide limits and may be within the range from 0.1 to 10,000 mol of additive per mole of catalyst. Preference is given to using from 0.5 to 5 mol per mole of catalyst. One or more additives may be used in any one reaction. The process of the invention is preferably carried out employing amines, especially tertiary amines, as additives.

The process of the invention is carried out either continuously or batchwise, preferably in the liquid phase and preferably in an organic solvent which is inert under reaction conditions, for example in the presence of ethers, such as diethyl ether, methyl tert-butyl ether, tetrahydrofuran and 1,4-dioxane, alkanols such as methanol, ethanol and isopropanol, hydrocarbons such as pentane, hexane and cyclohexane, also chlorinated hydrocarbons such as methylene chloride, chloroform and dichloroethane. The amount of solvent is generally within the range from 5 to 95% by weight of solvent, based on the reaction batch. The process of the invention is carried out continuously or batchwise in pressure-resistant reactors, such as stirred, tubular or loop reactors.

The process of the invention thus makes it possible for the rhodium complex used as catalyst for the synthesis of γ-butyrolactones from alkynes and CO to be repeatedly, and almost quantitatively each time, recovered simply by precipitation from the reaction effluent under hydrogenating conditions and to be reused with virtually the same activity and selectivity.

EXAMPLES

Example 1
(For Comparison)

The initial charge was 672 mg (2.6 mmol) of Rh(CO)$_2$acac, 2.25 g (22.3 mmol) of triethylamine and 32.8 g (1.8 mol) of water in 400 ml of dioxane. 8.2 l (0.31 mol) of acetylene were injected at room temperature with stirring to a pressure of 3.6 bar. The pressure was then raised to 200 bar with carbon monoxide. The reaction batch was heated to 120° C., raising the pressure to 248 bar, and subsequently stirred for 2 h. After cooling and reactor decompression, the effluent was worked up by distillation. Based on the amount of acetylene used, 52% of 2(5H)-furanone and 22% of butyrolactone had formed. The bottom product of the distillation, which contained the catalyst, was introduced as an initial charge in 400 ml of dioxane and admixed with 2.25 g (22.3 mmol) of triethylamine and 32.8 g (1.8 mol) of water. 8.2 l (0.31 mol) of acetylene were injected at room temperature to a pressure of 3.6 bar. The pressure was then raised to 200 bar with carbon monoxide. The reaction batch was heated to 120° C., raising the pressure to 248 bar, and subsequently stirred for 2 h. After cooling and reactor decompression, the reactor's effluent was worked up by distillation and the bottom product of the distillation, which contained the catalyst, reused. Altogether this procedure was repeated three times without addition of fresh catalyst. The respective yields of product of value (reported as the sum total of 2(5H)-furanone and butyrolactone) are shown in Table 1.

TABLE 1

Catalyst recycle after distillative workup

| Catalyst recycle | 0th | 1st | 2nd | 3rd |
|---|---|---|---|---|
| Yield of product of value [%] | 74 | 56 | 43 | 21 |

Example 2

The initial charge was 672 mg (2.6 mmol) of Rh(CO)$_2$acac, 2.25 g (22.3 mmol) of triethylamine and 32.8 g (1.8 mol) of water in 400 ml of dioxane. 8.2 l (0.31 mol) of acetylene were injected at room temperature with stirring to a pressure of 3.6 bar. The pressure was then raised to 200 bar with carbon monoxide. The reaction batch was heated to 120° C., raising the pressure to 248 bar, and subsequently stirred for 2 h. After cooling and reactor decompression, a sample was taken and analyzed by gas chromatography using the technique of the internal standard. Based on the amount of acetylene used, 59% of 2(5H)-furanone and 24% of butyrolactone had formed. 50 bar of hydrogen were then injected at room temperature and the reaction batch heated to 200° C. in the autoclave, raising the pressure to 89 bar. The pressure was then raised to 200 bar with hydrogen, which was followed by 1 h of stirring. After cooling and autoclave decompression the autoclave's effluent was filtered. The filtrate was found to contain only 1% of the rhodium used. The solid filter residue was reusable as catalyst. Following a distillative workup, butyrolactone was isolated in a yield of 81%, based on the amount of acetylene used.

Example 3

Example 2 was repeated, except that the hydrogenation reaction effluent was centrifuged. The centrifugate was worked up by distillation. The solid removed was introduced as an initial charge in 400 ml of dioxane and admixed with 2.25 g (22.3 mmol) of triethylamine and 32.8 g (1.8 mol) of water. 8.2 l (0.31 mol) of acetylene were injected at room temperature with stirring to a pressure of 3.6 bar. The pressure was then raised to 200 bar with carbon monoxide. The reaction batch was heated to 120° C., raising the pressure to 248 bar, and subsequently stirred for 2 h. After cooling and reactor decompression a sample was taken and analyzed by gas chromatography using the technique of the internal standard.

50 bar of hydrogen were then injected at room temperature and the reaction batch heated to 200° C. in the autoclave, raising the pressure to 89 bar. The pressure was then raised to 200 bar with hydrogen, which was followed by 1 h of stirring. After cooling and autoclave decompression the autoclave's effluent was again centrifuged to remove and reuse the catalyst. The centrifugate was worked up by distillation. The sequence of carbonylation/hydrogenation/catalyst removal/carbonylation was repeated altogether five times without addition of fresh catalyst. The distillative yields of butyrolactone obtained after each cycle, in each case based on the amount of acetylene used, are recited in Table 2 below:

| Catalyst recycle | 0th | 1st | 2nd | 3rd | 4th | 5th |
|---|---|---|---|---|---|---|
| Yield of product of value [%] | 81 | 79 | 82 | 83 | 78 | 81 |

We claim:

1. A process for producing butyrolactones of the general formula I

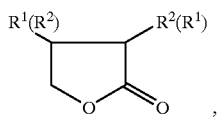

where $R^1$ and $R^2$ are each hydrogen, alkyl, hydroxyalkyl or unsubstituted or halogen-, alkoxy- and/or alkyl-substituted aryl or trialkylsilyl, by reacting alkynes of the general formula II

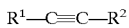 II, where $R^1$ and $R^2$ are each as defined above, with carbon monoxide and water in the presence of a homogeneous rhodium catalyst under pressures from 20 to 300 bar and hydrogenating the unhydrogenated 2(5H)-furanone intermediates, which comprises a) reacting the carbonylation reaction mixture with hydrogen at from 150 to 250° C. and from 100 to 300 bar,
b) removing the precipitated catalyst and returning it into the carbonylation reaction, and
c) subjecting the catalyst-free reaction mixture to a distillation to recover the butyrolactone.

2. A process as claimed in claim 1, wherein the hydrogenation (a) is carried out at from 180 to 230° C. and from 150 to 250 bar.

3. A process as claimed in claim 1, wherein the recovering of the catalyst in step (b) is effected by filtration, decanting or centrifugation.

4. A process as claimed in claim 1, wherein steps (a) to (c) are carried out continuously.

5. A process as claimed in claim 1, wherein the carbonylation reaction is carried out with not less than 4 equivalents of CO and not less than 2 equivalents of water.

6. A process as claimed in claim 1, wherein the carbonylation is carried out in the presence of an amine or of an ammonium salt.

7. A process as claimed in claim 1, wherein the carbonylation is carried out in the presence of a halide.

8. A process as claimed in claim 1, wherein the carbonylation is carried out in the presence of a polymerization inhibitor.

9. A process as claimed in claim 1, wherein the alkyne used is acetylene.

10. A process as claimed in claim 1, wherein the reaction with carbon monoxide and water is carried out at from 170 to 230 bar.

* * * * *